United States Patent [19]

Diehr et al.

[11] Patent Number: 5,693,821

[45] Date of Patent: Dec. 2, 1997

[54] PROCESS FOR THE PREPARATION OF SUBSTITUTED AMINOTRIAZOLINONES

[75] Inventors: Hans-Joachim Diehr, Wuppertal; Klaus-Helmut Müller, Düsseldorf; Reinhard Lantzsch, Wuppertal, all of Germany

[73] Assignee: Bayer Aktiengesellshcaft, Leverkusen, Germany

[21] Appl. No.: 696,013

[22] Filed: Aug. 12, 1996

[30] Foreign Application Priority Data

Aug. 18, 1995 [DE] Germany .................. 195 30 450.0

[51] Int. Cl.[6] .................................. C07D 249/12
[52] U.S. Cl. ........................................ 548/263.8
[58] Field of Search ............................ 548/263.8

[56] References Cited

U.S. PATENT DOCUMENTS 4,952,701  8/1990  Muller et al. ............... 548/263.8
5,057,144  10/1991  Daum et al. .

Primary Examiner—Patricia L. Morris
Attorney, Agent, or Firm—Sprung Kramer Schaefer & Briscoe

[57] ABSTRACT

The invention relates to a new process for the preparation of substituted aminotriazolinones of the general formula (I)

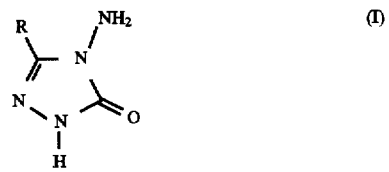

in which R has the meanings mentioned in the description.

6 Claims, No Drawings

PROCESS FOR THE PREPARATION OF SUBSTITUTED AMINOTRIAZOLINONES

The invention relates to a new process for the preparation of substituted aminotriazolinones, which are known as starting substances for herbicidally active compounds.

It has been disclosed that certain substituted aminotriazolinones, e.g. the compound 4-amino-5-methyl-2,4-dihydro-3H-1,2,4-triazol-3-one, are obtained when corresponding oxadiazolones, e.g. the compound 5-methyl-1,3,4-oxadiazol-2(3H)-one, are reacted with hydrazine hydrate in water (cf. EP 321833).

In this preparation procedure, the oxadiazolone is initially introduced in water and the hydrazine hydrate (in a high excess) is added thereto at room temperature and the mixture is then heated to boiling for a relatively long time. Excess hydrazine must be removed by distilling off and the desired aminotriazolinones are obtained in unsatisfactory yields and inadequate purity, so that a further purification step, e.g. azomethine formation, must follow.

It has now been found that substituted aminotriazolinones of the general formula (I)

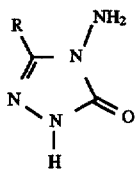

in which

R represents a radical of the series alkyl, alkoxy, alkylthio, alkylamino or dialkylamino, each of which is optionally substituted, are obtained in good yields and in high purity when hydrazine hydrate is initially introduced in the presence of a basic compound (optionally dissolved in water) and in the presence of a polar organic solvent at temperatures between 50° C. and 150° C., an oxadiazolone of the general formula (II)

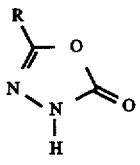

in which

R has the meaning indicated above, is slowly metered in within this temperature range and the reaction mixture is kept in the temperature range indicated above until the reaction is virtually complete.

Surprisingly, the substituted aminotriazolinones of the general formula (I) can be prepared in significantly higher yields and in substantially better quality than according to the prior art by the process according to the invention, in which the hydrazine hydrate can be employed in approximately equimolar amount.

The process according to the invention thus represents a valuable enrichment of the prior art.

The process according to the invention preferably relates to the preparation of compounds of the formula (I), in which R represents a radical of the series alkyl, alkoxy, alkylthio, alkylamino or dialkylamino each having up to 6 carbon atoms, each of which is optionally substituted by cyano, halogen or $C_1$–$C_4$-alkoxy.

The process according to the invention in particular relates to the preparation of compounds of the formula (I), in which R represents a radical of the series methyl, ethyl, n- or i-propyl, n-, i-, s- or t-butyl, n-, i-, s- or t-pentyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino, diethylamino or dipropylamino, each of which is optionally substituted by cyano, fluorine, chlorine, bromine, methoxy or ethoxy.

If, for example, 5-methyl-1,3,4-oxadiazol-2(3H)-one and hydrazine hydrate are used as starting substances, the course of the reaction in the process according to the invention can be outlined by the following equation:

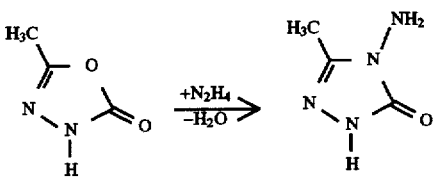

Formula (II) provides a general definition of the oxadiazolones to be used as starting substances in the process according to the invention for the preparation of the compounds of the formula (I). In formula (II), R preferably or in particular has that meaning which has already been given above as preferred or as particularly preferred for R in the description of the compounds of the formula (I) to be prepared according to the invention.

The oxadiazolones of the formula (II) are known and/or can be prepared by processes known per se (cf. EP 321833, Justus Liebigs Ann. Chem. 1973, 1816–1820).

The process according to the invention is carded out in the presence of a basic compound (optionally dissolved in water). Suitable basic compounds in this connection are in general the customary inorganic or organic bases or acid acceptors. These preferably include alkali metal or alkaline earth metal acetates, amides, carbonates, hydrogen carbonates, hydrides, hydroxides or alkoxides, for example sodium, potassium or calcium acetate, lithium, sodium, potassium or calcium amide, sodium, potassium or calcium carbonate, sodium, potassium or calcium hydrogen carbonate, lithium, sodium, potassium or calcium hydride, lithium, sodium, potassium or calcium hydroxide, sodium or potassium methoxide, ethoxide, n- or i-propoxide, n-, i-, s- or t-butoxide; furthermore also basic organic nitrogen compounds, for example trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]octane (DABCO), 1,5-diazabicyclo[4.3.0]-non-5-ene (DBN) and 1,8-diazabicyclo[5.4.0]-undec-7-ene (DBU).

Alkali metal hydroxides such as lithium hydroxide, sodium hydroxide and potassium hydroxide (in particular sodium hydroxide—optionally dissolved in water) are particularly preferably employed as basic compounds when carrying out the process according to the invention.

The process according to the invention is carried out in the presence of a polar organic solvent. These preferably include dialkyl ethers, for example diisopropyl ether, methyl t-butyl ether (MTBE), ethyl t-butyl ether, methyl t-pentyl ether (TAME), ethyl t-pentyl ether, tetrahydrofuran (THF), 1,4- dioxane, ethylene glycol dimethyl ether or diethyl ether, diethylene glycol dimethyl ether or diethyl ether; dialkyl ketones, for example butanone (methyl ethyl ketone), methyl i-propyl ketone or methyl i-butyl ketone, nitriles, for example acetonitrile, propionitrile, butyronitrile or benzonitrile; amides, for example N,N-dimethyl-formamide (DMF), N,N-dimethyl-acetamide, N-methyl-formanilide, N-methyl-pyrrolidone or hexamethyl-phosphoramide; esters, for example methyl, ethyl, n- or i-propyl, n-, i- or s-butyl acetate; alcohols, for example ethanol, n- or i-propanol, n-, i-, s- or t-butanol, as well as sulphoxides, for example dimethyl sulphoxide.

Alcohols, such as methanol, ethanol, n- or i-propanol, n-, i-, s- or t-butanol (in particular n-butanol) are particularly preferably employed as solvents in the process according to the invention.

When carrying out the process according to the invention, the reaction temperatures can be varied within a relatively wide range. In general, the process is carded out at temperatures between 50° C. and 150° C., preferably between 70° C. and 130° C., in particular between 90° C. and 110° C.

The process according to the invention is in general carried out under normal pressure. However, it is also possible to carry out the process according to the invention at elevated or reduced pressure—in general between 0.1 bar and 10 bar. When using low-boiling alcohols, the process is preferably carried out at elevated pressure.

To carry out the process according to the invention, in general between 0.8 and 1.5 mol, preferably between 0.9 and 1.2 mol, in particular between 1.0 and 1.1 mol, of hydrazine hydrate and between 0.01 and 1 mol, preferably between 0.05 and 0.50 mol, in particular between 0.10 and 0.25 mol, of basic compound are employed per mole of oxadiazolone of the formula (II).

The hydrazine hydrate is in general mixed at room temperature with the basic compound (optionally dissolved in water) and the polar organic solvent and the mixture is heated to the required reaction temperature. The oxadiazolone of the formula (II) is then slowly metered in and the reaction mixture is further kept in the temperature range indicated—if appropriate with stirring—until the reaction is virtually complete.

The working-up and isolation of the products of the formula (I) is problematical, as they dissolve in water very readily, but very sparingly in organic solvents. If, for example, the mixture—if appropriate after lowering the temperature—is diluted with water and adjusted to pH 7 by addition of an acid, for example hydrochloric acid or sulphuric acid, then the solvent and a part of the water are largely distilled off—if appropriate under reduced pressure, the desired product remains as a residue and can be isolated by filtering off, where, however, on account of the good water solubility a part of the product remains in the water and is lost.

In a preferred embodiment of the working-up, the pH is therefore adjusted to 7 by addition of an acid and the solvent used in the process, which is preferably immiscible or only slightly miscible with water, directly or alternatively continuously extracted with another suitable solvent at elevated temperature. The temperature is between 30° and 100° C., preferably between 45° and 90° C.

Besides the alcohols preferably used such as n- or iso-propanol, n-, iso-, sec- or tert-butanol, esters, for example methyl or ethyl acetate, can preferably be used for continuous extraction.

Surprisingly, the desired product is obtained quantitatively and in high purity. Product of the formula (I) is no longer contained in the water phase.

The substituted aminotriazolinones of the general formula (I) to be prepared by the process according to the invention have already been disclosed as starting substances for herbicidally active compounds (cf. EP 294 666, EP 370 293).

PREPARATION EXAMPLES

EXAMPLE 1

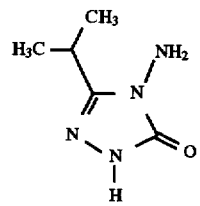

118.4 g (0.914 mol) of 5-i-propyl-1,3,4-oxadiazol-2(3H)-one are added dropwise with stirring in the course of about 25 minutes to a mixture, heated to 102° C. to 105° C., of 45.8 g (0.915 mol) of hydrazine hydrate, 12.2 g of 45% strength sodium hydroxide solution (0.137 mol of NaOH) and 460 ml of n-butanol and the reaction mixture is then kept in the temperature range between 100° C. and 105° C. for 3 hours. After cooling to about 50° C., it is diluted with 230 ml of water and the pH is then adjusted to 7 at about 20° C. by addition of about 45% strength sulphuric acid. The solvent is then largely distilled off, first at normal pressure, then at a pressure between 100 mbar and 110 mbar (bath temperature: about 60° C.), the residue which remains is dissolved in 230 ml of water at about 75° C., and the solution is cooled to 10° C. to 20° C. The product which is obtained in crystalline form in this process is isolated by filtering off, washed with 20 ml of ice-water and dried in a water-jet vacuum at 60° C.

105 g (purity: 98%, i.e. yield: 79% of theory) of 4-amino-5-i-propyl-2,4-dihydro-3H-1,2,4-triazol-3-one of melting point 171° C. are obtained.

EXAMPLE 2

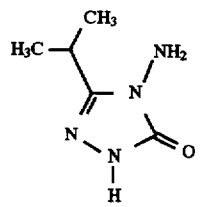

118.4 g (0.914 mol) of 5-i-propyl-1,3,4-oxadiazol-2(3H)-one are added dropwise with stirring in the course of about 25 minutes to a mixture, heated to 102° C. to 105° C., of 45.8 g (0.915 mol) of hydrazine hydrate, 12.2 g of 45% strength sodium hydroxide solution (0.137 mol of NaOH) and 460 ml of n-butanol and the reaction mixture is then kept in the temperature range between 100° C. and 105° C. for 3 hours. After cooling to about 20° C., it is diluted with 100 ml of water and adjusted to pH 7 using 33% strength hydrochloric acid. After addition of a further 200 ml of water, a clear two-phase mixture of butanol and water is obtained. By continuous extraction of the water phase with butanol at 80° C., all the reaction product can be collected in the organic phase, while the by-products formed in the reaction remain in the water.

By distilling off the butanol, 118 g (purity: 98.3%, i.e. yield 89.3% of theory) of 4-amino-5-i-propyl-2,4-dihydro-3H-1,2,4-triazol-3-one of melting point 171° C. are obtained.

It will be understood that the specification and examples are illustrative but not limitative of the present invention and that other embodiments within the spirit and scope of the invention will suggest themselves to those skilled in the art.

We claim:

1. A process for the preparation of a substituted aminotriazolinone of the formula

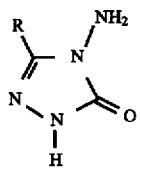

(I)

wherein

R represents a radical selected from the group consisting of alkyl, alkoxy, alkylthio, alkylamino or dialkylamino each having up to 6 carbon atoms, each of which is optionally substituted by cyano, halogen or $C_1$–$C_4$-alkoxy which comprises first, introducing hydrazine hydrate into the presence of a basic compound (optionally in the presence of water) and in the presence of a polar organic solvent at a temperature between 50° and 150° C., wherein said base is an inorganic or organic base, and second, slowly metering at said temperature range an oxadiazolone of the formula

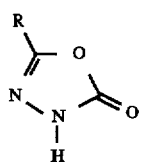

(II)

wherein

R has the meaning indicated above, and keeping the reaction mixture within this temperature range until the reaction is virtually complete.

2. The process for the preparation of a substituted aminotriazolinone according to claim 1, wherein R represents a radical selected from the group consisting of methyl, ethyl, n- or i-propyl, n-, i-, s- or t-butyl, n-, i-, s- or t-pentyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino, diethylamino or dipropylamino, each of which is optionally substituted by cyano, fluorine, chlorine, bromine, methoxy or ethoxy.

3. The process for the preparation of a substituted aminotriazolinone according to claim 1, wherein it is carried out at a temperature between 70° and 130° C.

4. The process of the preparation of a substituted aminotriazolinone according to claim 1, wherein the process is carried out under normal pressure.

5. The process for the preparation of a substituted aminotriazolinone according to claim 1, wherein per mole of oxadiazolone of the formula

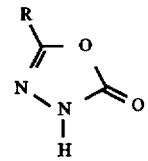

(II)

wherein R has the meaning indicated in claim 7, between 0.8 and 1.5 mol of hydrazine hydrate and between 0.01 and 1 mol of basic compound are employed.

6. The process for the preparation of a substituted aminotriazolinone according to claim 1, wherein the basic compound is an alkali metal or alkaline earth metal acetate, amide, carbonate, hydrogen carbonate, hydride, hydroxide or alkoxide or is a basic nitrogen compound.

* * * * *